US008312796B2

(12) United States Patent
Künkel et al.

(10) Patent No.: US 8,312,796 B2
(45) Date of Patent: Nov. 20, 2012

(54) MICROTOME

(75) Inventors: Stefan Künkel, Karlsruhe (DE); Frank Sauer, Wiesloch (DE); Volker Schneider, Sinsheim-Weiher (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 274 days.

(21) Appl. No.: 11/693,014

(22) Filed: Mar. 29, 2007

(65) Prior Publication Data

US 2007/0227330 A1 Oct. 4, 2007

(30) Foreign Application Priority Data

Mar. 30, 2006 (DE) ..................... 20 2006 005 259 U
May 26, 2006 (DE) ..................... 20 2006 008 329 U

(51) Int. Cl.
*B26D 7/06* (2006.01)
*B23D 19/00* (2006.01)
*B27B 5/18* (2006.01)

(52) U.S. Cl. .............................. 83/78; 83/703; 83/915.5

(58) Field of Classification Search ................. 83/915.5, 83/78, 703; 361/220
See application file for complete search history.

(56) References Cited

U.S. PATENT DOCUMENTS 4,217,185 A * 8/1980 Kyriacou et al. ............. 205/426
4,221,146 A 9/1980 Kindel et al.
4,602,310 A * 7/1986 Fenster ......................... 361/212
4,647,500 A * 3/1987 George et al. .............. 428/313.3
4,664,971 A 5/1987 Soens
4,716,294 A * 12/1987 Pettke et al. .................. 250/353
4,760,492 A * 7/1988 Walsh ........................... 361/214
4,814,698 A * 3/1989 St. Onge et al. ......... 324/754.15
4,866,565 A * 9/1989 Wray, Jr. ....................... 361/215
4,879,037 A * 11/1989 Utzinger ....................... 210/634
4,899,521 A * 2/1990 Havens ........................... 53/461
5,150,499 A * 9/1992 Berfield ....................... 15/327.1
5,282,404 A * 2/1994 Leighton et al. .................. 83/13
5,396,396 A * 3/1995 Watanabe ..................... 361/212
5,521,756 A 5/1996 Meier, Jr. et al.
5,589,119 A * 12/1996 Hetherington ................ 264/129
5,761,977 A * 6/1998 Jakobi et al. ....................... 83/13
6,123,990 A * 9/2000 Wiggins et al. ............... 427/242
6,287,450 B1 * 9/2001 Hradil ........................... 205/745
6,347,247 B1 * 2/2002 Dev et al. .......................... 607/2
6,464,413 B2 * 10/2002 Oyamada ...................... 396/575
6,865,416 B2 * 3/2005 Dev et al. .......................... 607/2
2001/0056143 A1 * 12/2001 Baumgaertel et al. ........ 524/364

(Continued)

OTHER PUBLICATIONS

Richards and Jenkins, "Static Electricity Elimination During Sectioning with a Microtome," Science, Jun. 9, 1950, vol. 111, Issue 2893, pp. 624-625.

(Continued)

*Primary Examiner* — Ghassem Alie
*Assistant Examiner* — Bharat C Patel
(74) *Attorney, Agent, or Firm* — Hodgson Russ LLP

(57) ABSTRACT

The present invention relates to a microtome (1) having functional regions to be operated manually, in particular a sample holder (2), a cutting device (3), a section removal system (4), and a section collection pan (5). A microtome (1) is described in which the particularly firm contact or adhesion of sectioning waste fragments and, in particular, of thin sections can be at least largely avoided. For this purpose, the microtome (1) according to the present invention is characterized in that the components of the microtome (1) that can be brought into contact with paraffin sections are embodied in electrically conductive fashion.

14 Claims, 2 Drawing Sheets

U.S. PATENT DOCUMENTS

| | | | | |
|---|---|---|---|---|
| 2004/0224590 | A1* | 11/2004 | Rawa et al. | 442/176 |
| 2004/0261597 | A1* | 12/2004 | Thiem et al. | 83/703 |
| 2005/0008809 | A1* | 1/2005 | Miller et al. | 428/40.1 |
| 2005/0115373 | A1* | 6/2005 | Kunkel | 83/168 |
| 2005/0171575 | A1* | 8/2005 | Dev et al. | 607/2 |

OTHER PUBLICATIONS

Jiangmen Yuxun Trading and Development Co. Ltd., Technical Data Sheet—GRILON® BS EC [online], published Dec. 14, 2004. Available from http://www.yuxun.cn/cn/grilon/BS_EC_E.pdf [Accessed Jun. 22, 2007].

Jiangmen Yuxun Trading and Development Co. Ltd., Technical Data Sheet—GRILAMID® LKN-5H [online], published Dec. 14, 2004. Available from http://www.yuxun.cn/cn/Grilamid/LKN-5H_E.pdf [Accessed Jun. 25, 2007].

* cited by examiner

MICROTOME

CROSS REFERENCE TO RELATED APPLICATIONS

This application claims priority of German utility model application 20 2006 005 259.3 filed Mar. 30, 2006 and German utility model application 20 2006 008 329.4 filed May 26, 2006, which are both incorporated by reference herein.

FIELD OF THE INVENTION

The present invention relates to a microtome having functional regions to be operated manually, in particular a sample holder, a cutting device, a section removal system, and a section collection pan.

BACKGROUND OF THE INVENTION

Microtomes of this kind are known from the existing art, for example from DE 103 52 578 B3, and are used predominantly for the production of thin paraffin sections in the fields of biology, medicine, and industrial research. The samples and preparations to be investigated are usually embedded in paraffin, in a preceding preparation process, into a specimen holding device, for example a carrier basket. A drive device that, by means of a relative motion, guides the sample, located in the specimen holding device, over a knife arranged on the microtome is provided for sectioning. The knife is generally horizontally displaceable in a knife holding device, and can be clamped in at an adjustable angle in defined fashion.

In so-called rotary microtomes, the drive device implements both the movement of the knife holding device in adjustable micrometer steps (referred to as horizontal advance) and the vertical sectioning motion, which is usually generated by a crank mechanism driven by a handwheel.

A trimming function can be provided in order to produce an optimum section surface. For this, the knife holding device can be manually directed onto the vertically movable specimen holding apparatus for first sectioning operations, via a trimming lever, in steps that are large as compared with the actual section thickness. Unusable sectioning waste occurs in this operation, and accumulates in a section collection pan of the microtome.

The samples to be investigated are often contaminated or bacterially infected biological material with which paraffin from the preparation process can be mixed. Even during ordinary sectioning of the samples with the microtome, fine sectioning waste unavoidably occurs; this drops down from the microtome knife and becomes deposited on portions of the microtome located therebelow, for example portions of its housing, in particular also in open gaps and especially in the section collection pan.

Because of the very complicated motion sequence, a complex mechanism is necessary on and in the microtome. Openings into the interior of the microtome, which are often covered with movable sliders, unavoidably remain at movement interfaces. Small slits, gaps, and openings in the microtome housing likewise occur, as a consequence of manufacture, in the vicinity of the aforesaid functional regions.

To prevent infection due to the contaminated sectioning waste, operating personnel are forced to intensively clean and disinfect the microtome and, in particular, the operating elements of the functional regions at relative short time intervals.

The section collection pan is particularly affected, since both the sectioning waste from trimming sections and the thin sections of contaminated samples that drop down build up in it. Large adhering sectioning waste fragments that are firmly in contact with the surface because of adhesion present a particular cleaning problem.

SUMMARY OF THE INVENTION

It is therefore the object of the present invention to solve the problems recited above and, in particular, to describe and further develop a microtome of the aforesaid kind in which firm contact or adhesion of sectioning waste fragments, and in particular of thin sections, can be at least largely avoided.

The microtome according to the present invention of the generic type achieves the aforesaid object by way of the features of Claim 1. According thereto, a microtome of this kind is characterized in that the components of the microtome that can be brought into contact with paraffin sections are embodied in electrically conductive fashion. The corresponding components should be embodied in such a way that their electrical conductivity remains substantially unchanged over time, i.e. ideally is permanently guaranteed.

What has been recognized according to the present invention is firstly that thin sections of contaminated samples, especially those dropping down, adhere very particularly firmly to housing portions of the microtome, and in particular to the section collection pan, if the housing portions of the microtome and/or the section collection pan are electrostatically charged. It is therefore proposed, in accordance with the present invention, that the components of the microtome that usually come into contact with paraffin sections and/or with sectioning waste be embodied in electrically conductive fashion. Ideally, therefore, all components that come into contact with paraffin sections and/or with sectioning waste are embodied in electrically conductive fashion. It could also be sufficient, however, to embody in electrically conductive fashion substantially and only the components of the microtome that most probably or most frequently come into contact with paraffin sections and/or with sectioning waste. By the fact that the relevant components are embodied in electrically conductive fashion, they should all be at a common electrical potential, and electrostatic charging of individual components of the microtome should accordingly be effectively avoided. It is thereby possible to decrease the possibility that, in particular, thin sections, paraffin sections, and/or sectioning waste becomes permanently or particularly firmly deposited onto individual components of the microtome because of electrostatic charging of the individual components, and can be removed again with difficulty or only with time-consuming cleaning efforts.

In particularly preferred fashion, therefore, housing portions of the microtome are embodied in electrically conductive fashion. In particular, housing portions of the cutting device, of the section removal system, and/or of the section collection pan could be embodied in electrically conductive fashion. Thus in addition to the internal components of the microtome, its housing portions can therefore additionally be embodied in electrically conductive fashion.

Very particularly preferably, the housing portions that on conventional microtomes are usually embodied from plastic are embodied in electrically conductive fashion. This refers in particular to the section collection pan, which hitherto has been fabricated in some circumstances from plastic and has had a coating containing silver ions and having an antimicrobial effect. Over time, however, a coating of this kind, which in some circumstances can likewise act in electrically antistatic fashion, can sooner or later be removed. The housing portions usually embodied from plastic can either be replaced by housing portions made of metal, or can be constituted by electrically conductive housing portions.

In a preferred embodiment, the housing portions of the microtome could thus comprise electrically conductive plastic. This could be implemented, in particular, in that the corresponding housing portions made of plastic comprise electrically conductive additions. Appropriate in this context, for example, are additions that could respectively comprise a metal mat, a steel fiber braid, a metal lattice, metal fibers, and/or a (permanent) metallic coating.

Very particularly preferably, at least one housing portion could comprise a plastic having the designation "Grilon BS EC." This plastic is a standard-viscosity, more heat-stabilized injection-molding PA6 grade having stainless steel fibers, this plastic exhibiting electrical conductivity or electrical antistatic properties in particular because of the stainless steel fibers. This plastic moreover exhibits thermoplastic properties with good impact toughness, and can be made light in color. This plastic is offered commercially, for example, by EMS Grivory or EMS-CHEMIE GmbH, Warthweg 14, 64823 Gross-Umstadt, Germany. Alternatively or additionally, at least one housing portion could be a plastic having the designation Antistatic-Equipped "Grilamid LKN-5H," of the same manufacturing company. Grilamid LKN-5H is a heat-stabilized polyamide-12 reinforced with 50% glass spheres. The properties of this injection-molding grade are: low water uptake, extremely dimensionally accurate, dimensionally stable, very little shrinkage, good sliding properties, and high abrasion strength.

The section collection pan could be embodied from (electrically conductive) metal, in particular stainless steel. Electrical conductivity would thereby exist for the section collection pan even without a coating.

In particularly preferred fashion, the microtome is embodied in antistatic fashion or comprises an antistatically embodied knife holder. This could be achieved, for example, in that at least one means with which the electrically conductively embodied components of the microtome are electrically connectable to one another is provided. The components electrically connected to one another can thereby be brought to a common electrical potential or grounded. Concretely, the means could comprise an electrically conductive cable 11.

The microtome according to the present invention could be embodied in the form of a rotary microtome or a sliding microtome or a rotating disc microtome.

BRIEF DESCRIPTION OF THE DRAWINGS

There are various ways of advantageously embodying and refining the teaching of the present invention. The reader is referred, for that purpose, on the one hand to the claims subordinate to Claim 1, and on the other hand to the explanation below of the preferred exemplifying embodiments of the invention with reference to the drawings. In conjunction with the explanation of the preferred exemplifying embodiments of the invention with reference to the drawings, an explanation is also given of generally preferred embodiments and refinements of the teaching. In the drawings:

In the Figures, identical or similar assemblies are labeled with the same reference characters. The microtome is described and further explained below with reference to an exemplifying embodiment depicted schematically in the drawings.

DETAILED DESCRIPTION OF THE INVENTION

Figure 1:
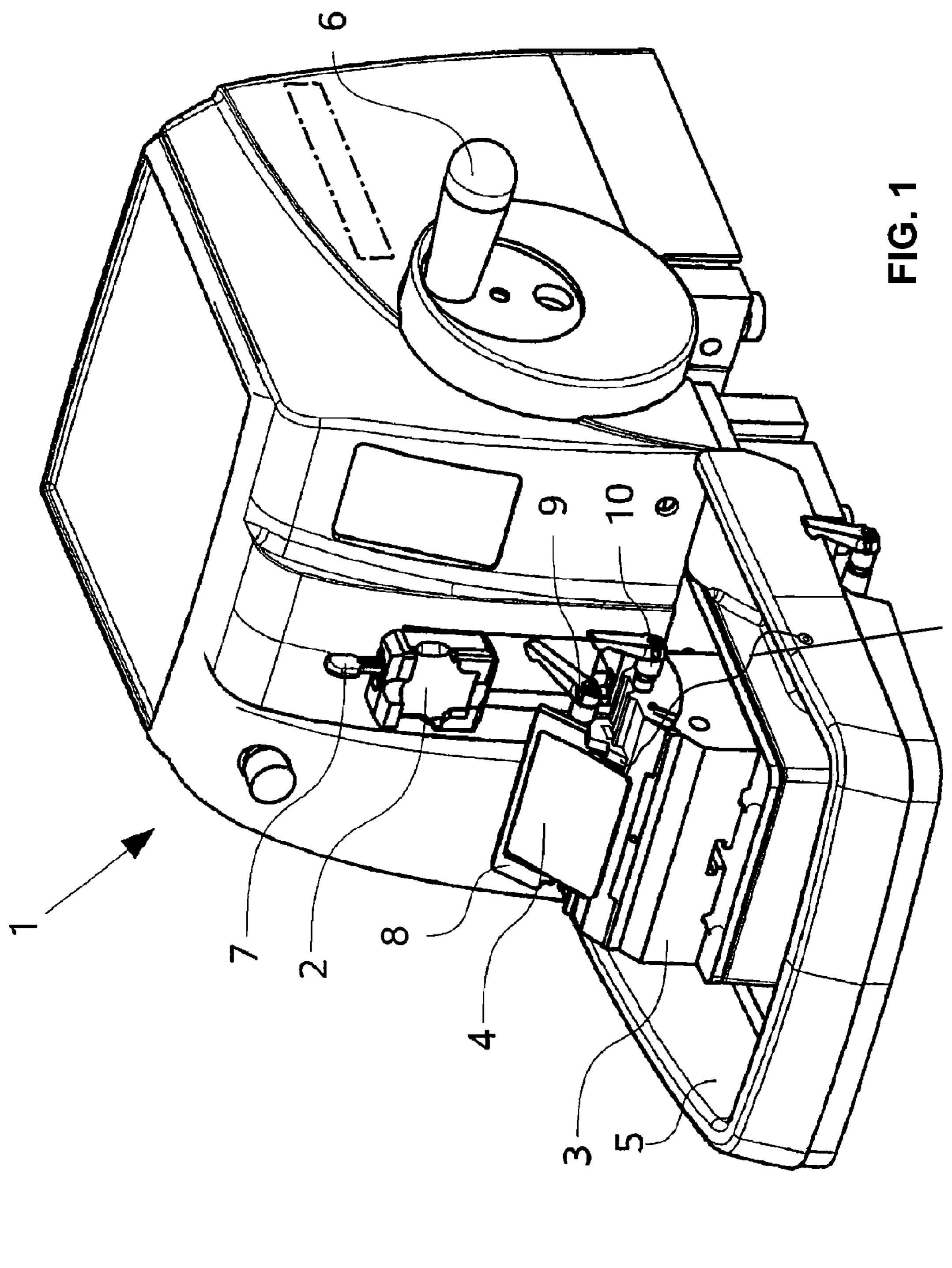
FIG. 1 is a schematic depiction of an exemplifying embodiment of a microtome according to the present invention.

FIG. 1 shows a rotary microtome 1 having functional regions to be operated manually, namely sample holder 2, cutting device 3, and section removal system 4. The sectioned material (not shown) dropping down from section removal system 4 is accumulated in a section collection pan 5. The up-and-down motion of sample holder 2, and the shifting of cutting device 3, are controlled by actuation of a hand crank 6 via a linkage (not further depicted).

The functional units are constructed from a plurality of structural elements. A clamping lever 7 is provided for rapid exchange of a sample carrier (not shown). Microtome knife 8 can also be aligned and immobilized in a pivotable knife receptacle by way of clamping shafts 9, 10. Cutting device 3 is mounted on concealed guidance rails.

Poorly accessible cavities and narrow slits and gaps, in which contaminated sectioned material can become deposited, are created for structural reasons when the numerous structural elements are fitted together. Contaminated material can also be transferred to hand crank 6 or to clamping lever 7 as a result of manipulation of the sample in functional regions 2, 3, 4, 5. These functional regions in particular can therefore come into contact with thin sections, sectioning waste, and/or paraffin sections. At least these functional regions of rotary microtome 1 are accordingly embodied, according to the present invention, in electrically conductive fashion, so that electrostatic charging of, for example, section collection pan 5 with respect to the remaining assemblies of rotary microtome 1 is at least largely preventable, since section collection pan 5 is in electrically conductive contact with at least one further component of rotary microtome 1 that is likewise electrically conductive.

Figure 2:
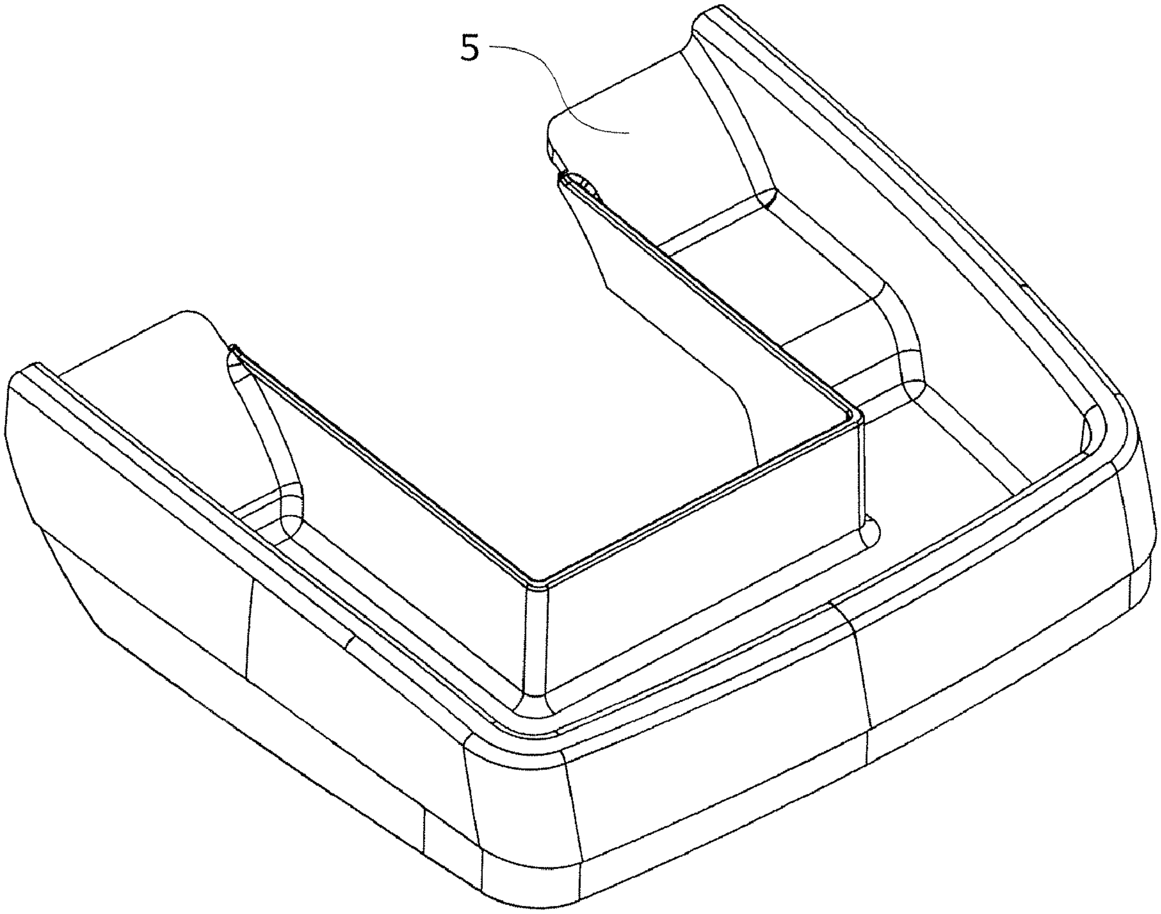
FIG. 2 is a schematic depiction of a section collection pan of the microtome of FIG. 1.

FIG. 2 is a perspective view showing section collection pan 5 of rotary microtome 1 of FIG. 1, in the removed state. Section collection pan 5 is embodied substantially in a U shape, and is made of plastic having the designation Antistatic-Equipped Grilamid LKN-5H, which can additionally be equipped with a steel fiber braid (although this is not shown in FIG. 2).

Although a rotary microtome is shown in FIGS. 1 and 2, let it be very particularly emphasized at this juncture that the present invention and the embodiment of a microtome associated therewith can also encompass a slide microtome, a rotating disc microtome, or a vibratome.

In conclusion, be it noted very particularly that the exemplifying embodiments discussed above serve merely to describe the teaching claimed, but do not limit it to the exemplifying embodiments.

What is claimed is:

1. A microtome comprising a plurality of functional regions to be operated manually, the plurality of functional regions including a sample holder (2), a cutting device (3), section removal system (4), and section collection pan (5);

an antistatic knife holder holding a knife (8);

a connecting cable electrically connecting the antistatic knife holder to the section collection pan (5);

wherein the section collection pan (5) is arranged for contact with paraffin sections cut by the microtome and the section collection pan is an electrically conductive structural element comprising electrically conductive plastic, whereby electrostatic charging of the section collection pan is prevented;

wherein the section collection pan comprises plastic comprised of a heat-stabilized polyamide (12) reinforced with 50% glass spheres;

wherein the antistatic knife holder, the connecting cable, and the section collection pan are electrically connected to one another and have a common electrical potential.

2. The microtome according to claim 1, wherein a housing portion in the region of the cutting device (3) is an electrically conductive structural element.

3. The microtome according to claim 2, wherein the housing portion in the region of the cutting device (3) comprises electrically conductive plastic.

4. The microtome according to claim 1, wherein a housing portion in the region of the section removal system (4) is an electrically conductive structural element.

5. The microtome according to claim 4, wherein the housing portion in the region of the section removal system (4) comprises electrically conductive plastic.

6. The microtome according to claim 1, wherein a housing portion in the region of the cutting device (3) and a housing portion in the region of the section removal system (4) are further electrically conductive structural elements.

7. The microtome according to claim 6, wherein each of the housing portions comprises a plastic having stainless steel fibers or a heat-stabilized polyamide (12) reinforced with 50% glass spheres.

8. The microtome according to claim 1, wherein the microtome includes housing portions made of plastic comprising an electrically conductive addition.

9. The microtome according to claim 8, wherein the electrically conductive addition to the plastic includes a metal mat.

10. The microtome according to claim 8, wherein the electrically conductive addition to the plastic includes a steel fiber braid.

11. The microtome according to claim 8, wherein the electrically conductive addition to the plastic includes a metal lattice.

12. The microtome according to claim 8, wherein the electrically conductive addition to the plastic includes metal fibers.

13. The microtome according to claim 8, wherein the electrically conductive addition to the plastic includes a metallic coating.

14. The microtome according to claim 1, wherein the microtome is selected from a group consisting of a rotary microtome, a sliding microtome, and a rotating disc microtome.

* * * * *